(12) United States Patent
Johnnie et al.

(10) Patent No.: US 8,976,241 B1
(45) Date of Patent: Mar. 10, 2015

(54) SURFACE DEFORMATION IMAGE ANALYZER

(71) Applicants: Nathan Johnnie, Middletown, RI (US); Francis J O'Brien, Jr., Newport, RI (US); Susan E Maloney, New Bedford, MA (US); Joseph W Robicheau, Portsmouth, RI (US)

(72) Inventors: Nathan Johnnie, Middletown, RI (US); Francis J O'Brien, Jr., Newport, RI (US); Susan E Maloney, New Bedford, MA (US); Joseph W Robicheau, Portsmouth, RI (US)

(73) Assignee: The United States of America as represented by the Secretary of the Navy, Washington, DC (US)

( * ) Notice: Subject to any disclaimer, the term of this patent is extended or adjusted under 35 U.S.C. 154(b) by 415 days.

(21) Appl. No.: 13/628,669

(22) Filed: Sep. 27, 2012

(51) Int. Cl.
*H04N 7/18* (2006.01)
*G06K 9/00* (2006.01)
*G01B 13/00* (2006.01)

(52) U.S. Cl.
CPC . *G01B 13/00* (2013.01); *H04N 7/18* (2013.01)
USPC .......................................................... 348/135

(58) Field of Classification Search
CPC ..... H04N 7/18; H04N 5/3532; H04N 9/3147; H04N 9/3185; H04N 9/3197
USPC ............................................................ 348/135
See application file for complete search history.

(56) References Cited

U.S. PATENT DOCUMENTS

| | | | |
|---|---|---|---|
| 5,142,588 A * | 8/1992 | Sogabe et al. | 382/141 |
| 2003/0112132 A1* | 6/2003 | Trajkovic et al. | 340/435 |
| 2010/0214406 A1* | 8/2010 | Potapenko | 348/135 |
| 2011/0211065 A1* | 9/2011 | Furui | 348/135 |
| 2011/0235089 A1* | 9/2011 | Xu et al. | 358/1.15 |
| 2013/0033596 A1* | 2/2013 | Crothers et al. | 348/135 |
| 2013/0038718 A1* | 2/2013 | Nakagome | 348/135 |

* cited by examiner

*Primary Examiner* — Christopher S Kelley
*Assistant Examiner* — Asmamaw G Tarko
(74) *Attorney, Agent, or Firm* — James M. Kasischke; Michael P. Stanley

(57) ABSTRACT

A device is provided with integrated hardware and software components for measuring and monitoring abnormalities on animal and human tissue and other surfaces. The device includes a display panel and a control panel secured to the upper surface of a housing and a plurality of sensor arrays attached to the lower surface on two scanner belts. A processor receives input from the sensor arrays to create data objects which are stored in an image object database. A retrieval component retrieves the image objects and identifies attributes to display image and quantitative values on a the display panel. A hardware processing component runs at least one algorithm to determine the area of a surface abnormality. Another hardware processing component is provided to receive user input to update images and to select a deformation region for area calculation.

11 Claims, 12 Drawing Sheets

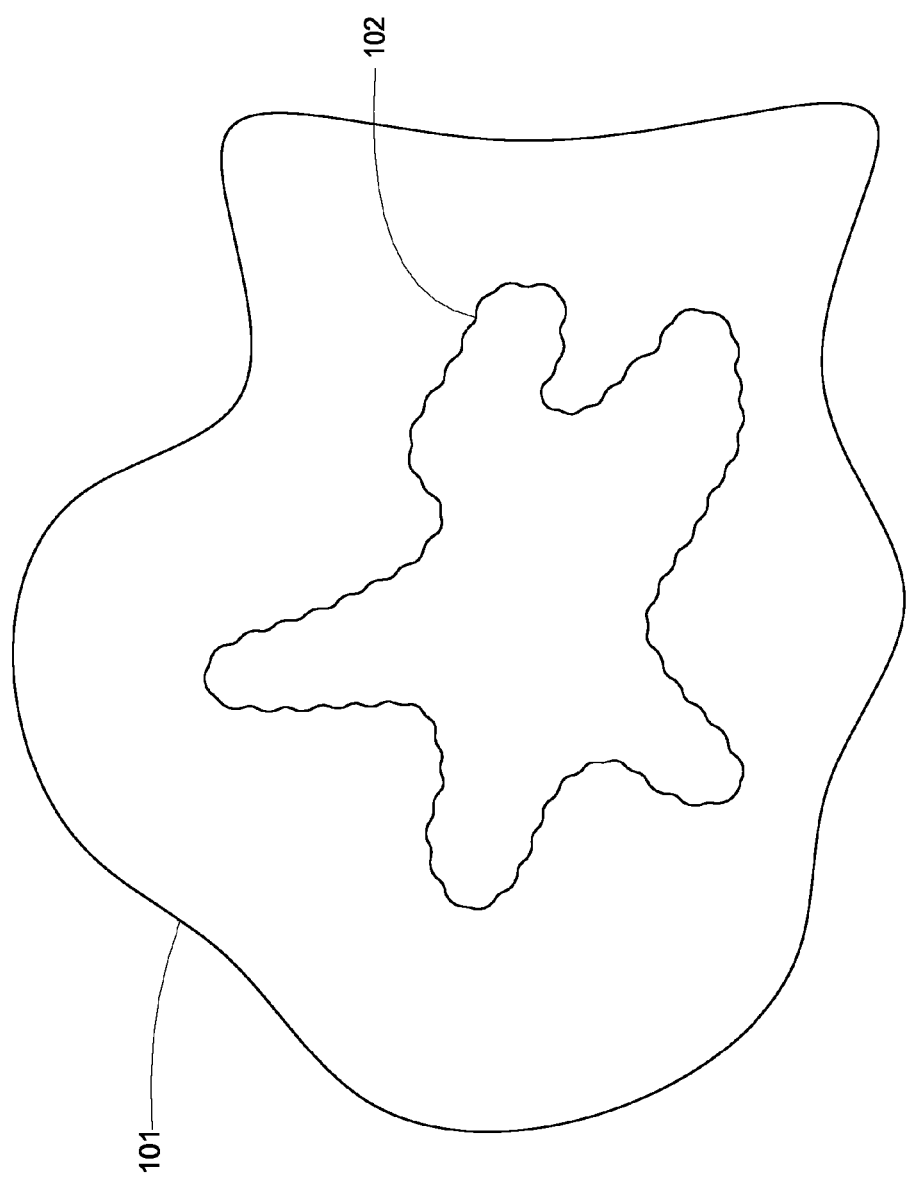

SURFACE DEFORMATION IMAGE ANALYZER

STATEMENT OF GOVERNMENT INTEREST

The invention described herein may be manufactured and used by or for the Government of the United States of America for Governmental purposes without the payment of any royalties thereon or therefore.

CROSS REFERENCE TO OTHER PATENT APPLICATIONS

None.

BACKGROUND TO THE INVENTION (1) Field of Invention

The present invention relates to the field of medical and laboratory equipment, and specifically to a device for analyzing deviations in hard surfaces, tissue and other surfaces.

(2) Description of the Prior Art

Magnification technologies known in the art to inspect solid surfaces have been used to aid in surface deformation analysis. However, these methods were not specifically developed for scanning a surface in detail in order to determine the existence of a surface abnormality and to provide diagnostic information, such as depth, density or other quantifiable properties.

One problem is that surface deformations and abnormalities which require precise measurement and comparison cannot be accurately diagnosed by visual inspection of images, and the cause of a deformation or repair suggestions may be highly subjective.

For example, a minute crack in a battery casing may be caused by physical strain on the casing or by chemical exposure. Because repair techniques for each cause may differ (e.g., adding structural support or adding a chemical-resistant coating); it is important to determine the cause of a surface deformation. Current magnification technologies do not provide sufficient analytical detail to make such diagnoses.

Similarly, magnetic resonance imaging (MRI) and magnification technologies for obtaining detailed diagnostic images are known in the art and have been adapted to identify variations in skin and tissue surfaces. However, these methods were not specifically developed for measuring skin surface abnormalities and have significant diagnostic limitations with respect to analyzing diagnostically significant surface variations.

Existing medical imaging technologies, such as MRI, positron emission tomography (PET) and ultrasound, provide detailed images of abnormalities used for diagnosis and treatment. These tools, however, require visual interpretation and analysis by a user attempting to diagnose or monitor a condition. The user may supplement the visual analysis by using additional image analysis software. Any visual interpretation and analysis allows for introduction of errors and subjective diagnostic conclusions. Additionally, when monitoring a condition, comparison of images over time is laborious if not impossible.

For example, human and animal tissue (including skin and internal tissue) develop a wide range of complex and subtle abnormalities which may not be accurately diagnosed by visual inspection. A single abnormality may (based on an MRI image) appear to be an abrasion when the abnormality is a cancerous growth. Similarly, a particular lesion may be caused by sun exposure, chemical exposure, or weakened immunity. Without analyzing the lesion in more detail, it may be difficult to determine the exact cause of the lesion and to provide the proper treatment.

Another problem is that there is no accurate way to monitor the changing characteristics of a surface deformation during repair or healing other than taking successive images; visually comparing them; or making multiple measurements for comparison. However, these methods are prone to inaccuracies because the methods require technicians to subjectively identify an area to capture for each image through their own visual observation. There are no known hardware devices which can accurately monitor a defined area. Wound tracing, saline-volume determinations and biochemical markers alternative methods have been used to monitor the healing process. These methods are similarly problematic, as the methods require direct physical contact with a wound.

It is therefore desirable to have a device which accurately measures surface deformations and eliminates the error caused by subjective and inconsistent evaluation of images in the attempted diagnosis of abnormalities. It is further desirable to have a device and method of use which yields information that can monitor the effectiveness of treatment and shorten the time frame and cost for treating non-healing wounds.

SUMMARY OF THE INVENTION

The present invention provides a device which includes integrated hardware and software components to measure and monitor surface abnormalities and deformations on solid surfaces and animal and human tissues. The device includes a display panel and a control panel secured to the upper surface of a housing. A plurality of sensor arrays, including a displacement sensor array, temperature sensor array, ultrasonic sensor array and ultraviolet sensor array, are attached to the lower surface of the housing on two scanner belts. The angle of the sensor arrays relative to the housing may be adjusted by using a primary adjustment element.

A processing component receives input from the sensor arrays to create a plurality of data objects which are stored in an image object database. A retrieval hardware processing component retrieves image objects from the image object database and identifies attributes to display an image and quantitative values on the display panel. An area hardware processing component runs at least one algorithm to determine the area of a surface abnormality. In some embodiments, a further hardware processing component may be provided to receive user input in order to update images and to select a deformation region for area calculation.

BRIEF DESCRIPTION OF THE DRAWINGS

FIG. 8A is an exemplary irregular deformation which may be scanned using the surface deformation image analyzer;

TERMS OF ART

Figure 1:
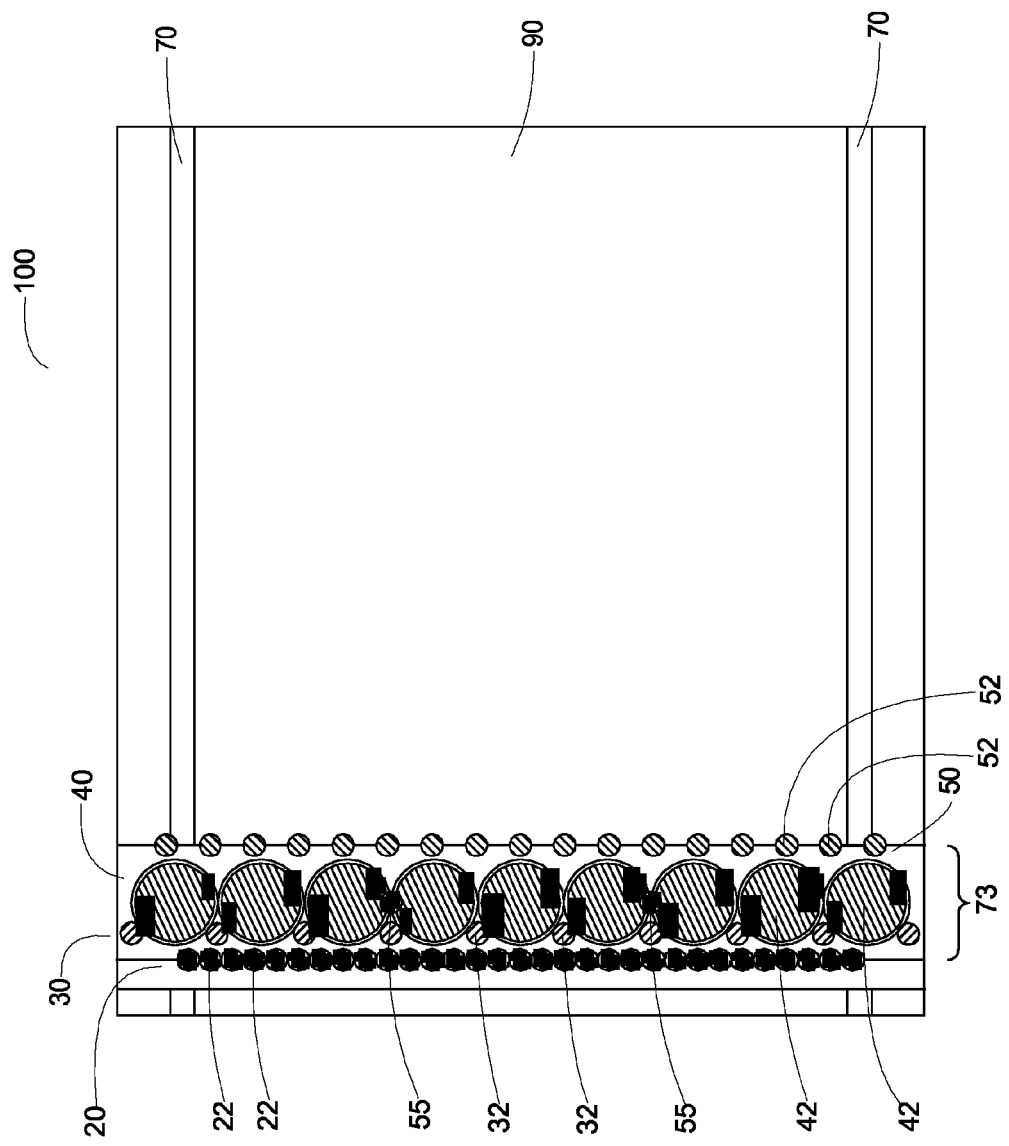
FIG. 1 is a bottom view of an exemplary embodiment of sensor arrays for a surface deformation image analyzer.

As used herein, the term "data object" refers to a data structure which includes data, functions or both, or which invokes functions when data is changed.

The term "deformation region" refers to an area of a surface having an inconsistent surface characteristic. For example, a deformation region may include, but is not limited to, a cut, crack, intrusion, protrusion, strain, scar, abrasion, birthmark, mole, discoloration, puncture, bump, rough texture, smooth texture, fracture, difference in temperature, and other surface characteristic or combination of characteristics.

The term "Human-Machine Interface" or "HMI" refers to a structure adapted to relay information between (to or from) a computer component or computer system and a human user or to store information which may be retrieved and/or manipulated by the human user.

The term "non-deformation region" refers to the non-deformed portion of a surface which is adjacent to a deformed surface and which is captured based on an algorithm used for calculating the area of the surface to be analyzed. A non-deformation region does not contain significant surface deformation.

The term "Pick's theorem" refers to a method of calculating the area of a polygon based on the number of grid points located within and on the perimeter of the polygon. Pick's theorem uses the equation $$\text{Area} = r^2 \left( i + \frac{b}{2} - 1 \right)$$

where i is the number of grid points located within the polygon, b is the number of grid points located on the perimeter of the polygon, and r is the scaling factor. The term "Pick's theorem polygon" refers to a polygon created for the purpose of performing an area calculation using Pick's theorem.

The term "sensor" refers to any structure that measures a physical property, such as temperature, displacement, reflections, and combinations of these and other properties, and converts the measured physical property into a signal to be processed and read by an observer. The term "sensor array" refers to a plurality of similar sensors operatively coupled to work in cooperation.

The term "Simpson's rule" refers to a method of calculating the area under a closed polynomial curve. When calculating an area relative to an x axis, Simpson's rule uses the equation $$\text{Area} = \int_a^b f(x)\,dx \approx \frac{h}{3}[y_0 + 4y_1 + 2y_2 + \ldots + 4y_{n-1} + y_n]$$

where $y_i$ are variable heights lying perpendicular to the x axis and h=b−a/n is the length of the curve divided into n even numbered partitions. When calculating an area relative to a y axis, Simpson's rule uses the equation $$\text{Area} = \int_c^d f(y)\,dy \approx \frac{h}{3}[x_0 + 4x_1 + 2x_2 + \ldots + 4x_{n-1} + x_n]$$

where $x_1$ are variable heights lying perpendicular to the y axis and $$h = \frac{d-c}{n}$$

is the length of the curve divided into r even numbered partitions.

The term "surface deformation" refers to any abnormality on a surface. Surface deformations may be two- or three-dimensional deformations, including, but not limited to; protrusions, intrusions, cracks, punctures, abrasions, areas of discoloration, areas of temperature variation, cuts, strains, scars, birthmarks, moles, bumps, rough textures, punctures, smooth textures, and combinations of these and other abnormalities.

DETAILED DESCRIPTION OF INVENTION

For the purpose of promoting an understanding of the present invention; references are made in the text to exemplary embodiments of software that can process, smooth, and grid bathymetric data into a uniform distribution data set. It should be understood that no limitations on the scope of the invention are intended by describing these exemplary embodiments. One of ordinary skill in the art will readily appreciate that alternate but functionally equivalent bathymetric mapping software may be used. The inclusion of additional elements may be deemed readily apparent and obvious to one of ordinary skill in the art. Specific elements disclosed herein are not to be interpreted as limiting, but rather as a basis for the claims and as a representative basis for teaching one of ordinary skill in the art to employ the present invention. It should be understood that the drawings are not necessarily to scale; instead, the drawings emphasize the principles of the invention. In addition, in the embodiments depicted herein, reference numerals in the various drawings refer to identical or near identical structural elements.

The method for identifying a uniform distribution data set for producing bathymetric surface maps enhances the accuracy of measurements by using processing components to characterize changes in bathymetric data. The software can characterize changes in bathymetric data by using a grid pattern that contains a plurality of grid nodes and by processing data corrupted by outliers and measurement errors.

FIG. 1 is a bottom view of an exemplary embodiment of a sensor for a surface deformation image analyzer 100. In the exemplary embodiment shown, the image analyzer 100 contains four primary sensor arrays: a displacement sensor array 20, a temperature sensor array 30, an ultrasonic sensor (transducer) array 40, and an ultraviolet image sensor array 50 which includes digital cameras 55. These sensor arrays are arranged parallel to one another and perpendicular to scanner belts 70. The scanner belts 70 move the sensor arrays along a housing 90 in order to complete a scan of an area of interest.

The sensor arrays 20, 30, 40 and 50 are secured on an array assembly 73 to move in coordinated unison with the scanner belts 70. In the exemplary embodiment shown, the array assembly 73 is the structure securing the sensor arrays 20, 30, 40 and 50 and engaging the scanner belts 70.

As illustrated, the displacement sensor array 20 includes multiple displacement sensors 22 placed in parallel across the image analyzer 100. In the exemplary embodiment shown, the displacement sensors 22 are laser displacement sensors. However, in other exemplary embodiments, the displacement sensors may be any sensor which measures displacement.

During operation, the displacement sensors 22 are activated sequentially to ensure sensor readings are not corrupted by adjacent sensor emissions. Ultimately, the frames captured during scanning are fused together to make a cohesive image from the displacement sensor array 20. Sequential activation of the displacement sensors 22 and the scanning speed of the image analyzer 100 are coordinated to ensure image processing is not compromised.

In the exemplary embodiment shown, there are thirty-one displacement sensors 22 arranged in a continual line perpendicular to the scanner belts 70. The displacement sensors 22 are positioned so that each is in physical contact with the next in order to provide continual measurements across the displacement sensor array 20 and to avoid gaps in measurements. In further exemplary embodiments, the number and positioning of the displacement sensors 22 may vary—based on the size of a housing 90 or sized to achieve a desired level of accuracy in measuring an area of interest.

The temperature sensor array 30 is an array of multiple temperature sensors 32. In the exemplary embodiment shown, the temperature sensors 32 are laser temperature sensors. However, in further exemplary embodiments, the temperatures sensors 32 may be any sensor known in the art which measures temperature. Each temperature sensor 32 measures the produced or absorbed temperature of an area of interest. The temperature readings from each sensor 32 are fused to produce a spectrographic image.

In the exemplary embodiment shown, there are ten temperature sensors 32 arranged in a line perpendicular to the scanner belts 70. The temperature sensor array 30 is parallel with the displacement sensor array 20. The temperature sensors 32 are positioned to achieve accurate readings across the surface of an area of interest. In further exemplary embodiments, the number and positioning of the temperature sensors 32 may vary—based on the size of the housing 90 or to achieve a desired level of accuracy in measuring an area of interest. In some exemplary embodiments, an infrared heat sensing camera or array of cameras may be used in place of or in conjunction with the temperature sensor array 30.

Depending on the surface of interest and the type of deformation anticipated; it may be helpful to treat the surface of interest with a heat source, such as radiant heat, or cooling treatment, such as liquid nitrogen. Surface deformations or abnormalities may be more visible after being subject to the change in temperature. In some exemplary embodiments, the surface deformation image analyzer 100 may directly include a heating or cooling component.

The ultrasonic sensor array 40 includes a plurality of ultrasonic sensors 42. The ultrasonic sensors 42, or transducers, are active for the duration of a scan; unlike the displacement sensors 22 which are activated sequentially. In the exemplary embodiment shown, the operating frequency of each ultrasonic sensor 42 is unique to ensure there is no interference from neighboring transducers 42.

In the exemplary embodiment shown, there are nine ultrasonic sensors 42 arranged in a line perpendicular to the scanner belts 70 and parallel with the displacement sensor array 20 and the temperature sensor array 30. The ultrasonic sensors 42 are positioned so that each sensor is in physical contact with the next in order to provide continual readings across the ultrasonic sensor array 40. In further exemplary embodiments, the number and positioning of the ultrasonic sensors 42 may vary—based on the size of the housing 90 or to achieve a desired level of accuracy in measuring an area of interest.

The digital cameras 55 are arranged along the ultrasonic sensor array 40. In the exemplary embodiment shown, the digital cameras 55 are high-resolution, high-speed digital cameras and work in conjunction with the ultraviolet image sensor array 50. The ultraviolet image sensor array 50 is made of a plurality of ultraviolet LEDs 52. The ultraviolet light provided by the ultraviolet LEDs 52 ensures visual detection by the digital cameras 55 of otherwise invisible organic material on the area of interest. For example, a defect may be otherwise invisible but by the presence of organic material is made visible by the ultraviolet image sensor array 50 and is captured by the digital cameras 55.

In the exemplary embodiment shown, there are two digital cameras 55 arranged within the ultrasonic sensor array 40 and seventeen ultraviolet LEDs 52 positioned in a line parallel with the displacement sensor array 20, the temperature sensor array 30, and the ultrasonic sensor array 40. In further exemplary embodiments, more or fewer digital cameras 55 or ultraviolet LEDs 52 may be used for more detailed imaging. In still further exemplary embodiments, the arrangement of the ultraviolet LEDs 52 and the digital cameras 55 may vary in order to provide accurate and detailed imaging of an area of interest.

The housing 90 is illustrated as primarily rectangular with the scanner belts 70 running parallel to one another, and perpendicular to the sensor arrays 20, 30, 40 and 50, along one length of the housing. In the exemplary embodiment shown, the scanner belts 70 are half-rotational belts. The speed of scanner belts 70 is programmable to be coordinated with the functions of the sensor arrays 20, 30, 40 and 50. In further exemplary embodiments, the housing 90 may be configured differently and the scanner belts 70 may be oriented differently on the housing in order to accommodate different housing shapes. In still further exemplary embodiments, the scanner belts 70 may be positionable along the housing 90 to accommodate a specific area of interest.

Figure 2:
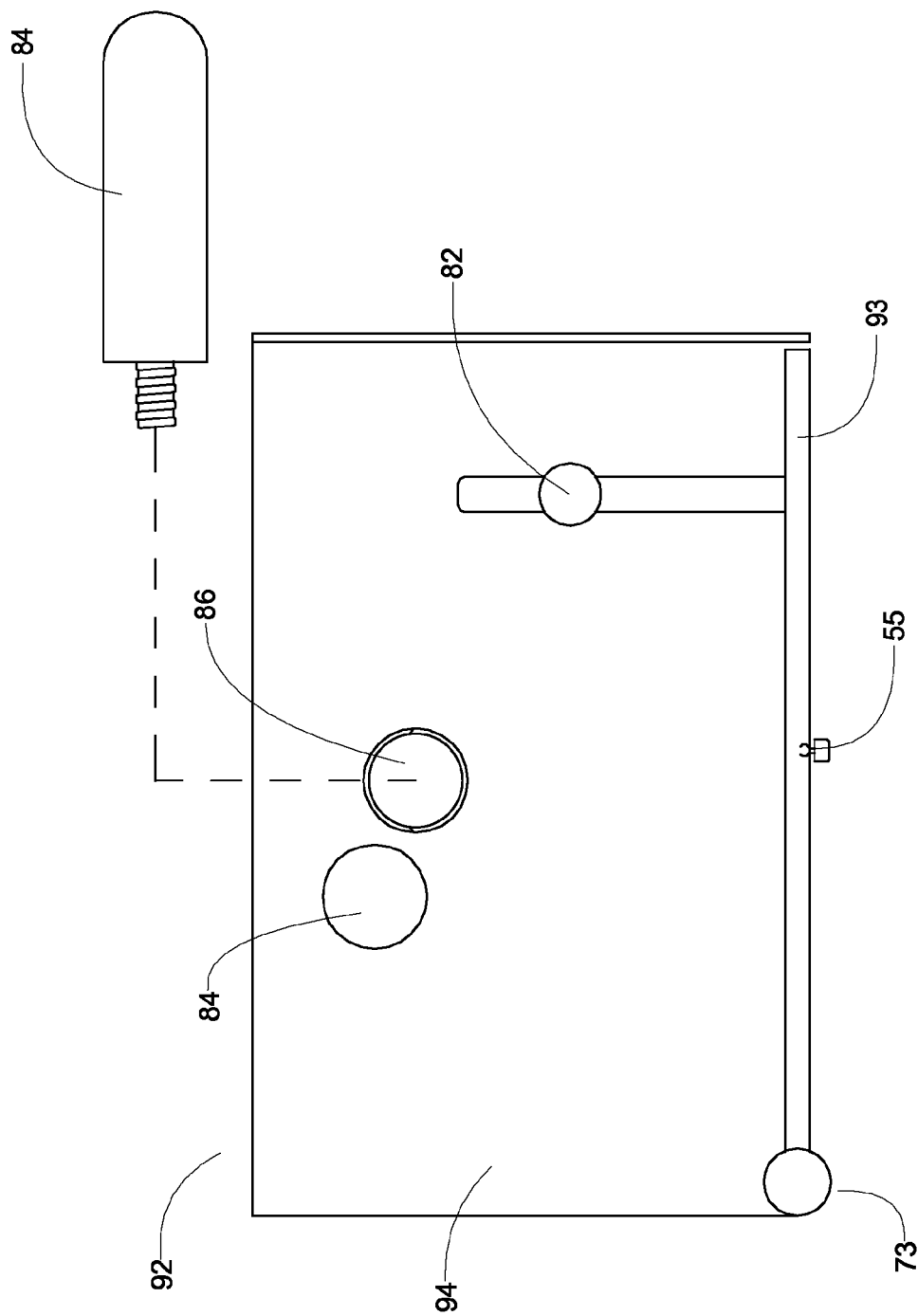
FIG. 2 is a side view of an exemplary embodiment of a sensor for the surface deformation image analyzer.

FIG. 2 is a side view of an exemplary embodiment of a sensor for the surface deformation image analyzer 100. A top surface 92 contains Human-Machine Interface (HMI) 200 (not shown), which includes sensor controls and sensor indicators and displays images to be analyzed. A side surface 94 contains primary element adjustment 82 and handles 84. The array assembly 73 and the digital camera 55 are visible along a bottom surface 93 of the housing 90.

The primary element adjustment 82 is used to alter the angle declination of the bottom surface 93 or the array assembly 73 when the surface of interest is not sufficiently flat for accurate measurements. The angle of declination of the bottom surface 93 may be adjusted up to approximately fifty degrees relative to the housing 90. An adjustable angle of declination up to at least forty-five degrees is preferred.

In the exemplary embodiment illustrated, a single primary element adjustment 82 is provided to cause one end of the bottom surface 93 to move downward; thereby, causing an angle of declination. In further exemplary embodiments, additional primary element adjustment components may be used to allow the bottom surface 93 to angle at any end.

In the exemplary embodiment shown, the primary element adjustment 82 is a slide which adjusts the angle of declination of the bottom surface 93 or the array assembly 73. In further exemplary embodiments, the angle of array assembly 73 relative to a surface of interest may be adjusted through any means known in the art. In further exemplary embodiments, the bottom surface 93 may also be adjusted closer or further from a surface of interest. The bottom surface 93 may be adjusted to between 0 and 45 centimeters, relative to the bottom of the housing 90.

The handles 84 are contoured rods which are removably attached to the side surface 94. In some embodiments, the handles 84 may be ergonomically contoured or include gripping or cushioned coatings to help a user grab the housing 90. In the exemplary embodiment shown, the handles 84 are threaded to engage threaded apertures 86 and secure to the housing 90. In further exemplary embodiments, the handles 84 may secure to the housing 90 through any means known in the art to provide a secure, though releaseable, connection, including, but not limited to, contours, pins, bolts, brackets, screws, and combinations thereof. In some exemplary embodiments, the handles 84 may be secured to any side of the housing 90.

Figure 3:
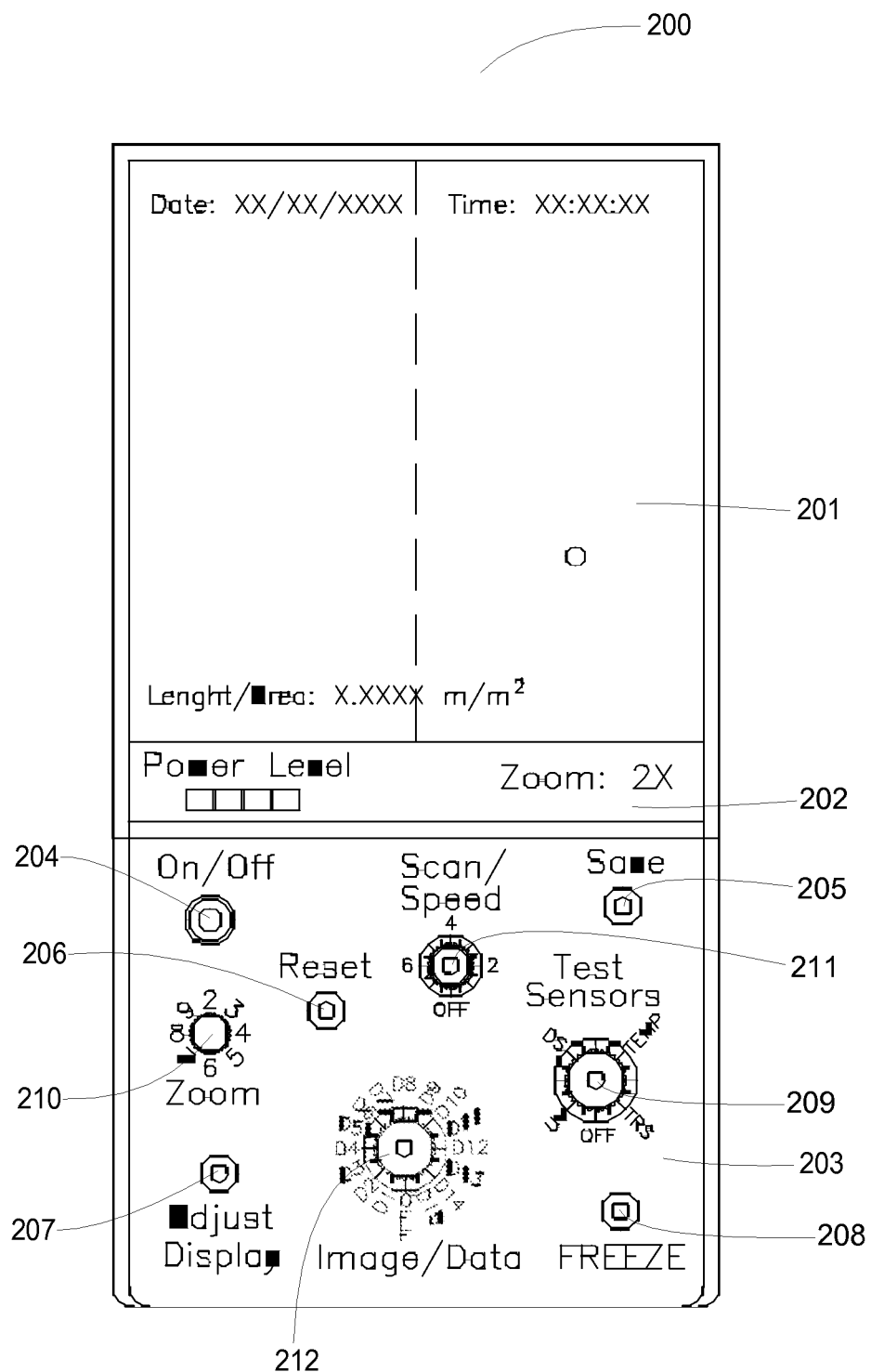
FIG. 3 is an exemplary embodiment of a human-machine interface for the surface deformation image analyzer.

FIG. 3 is an exemplary embodiment of the Human-Machine Interface (HMI) 200 for the surface deformation image analyzer 100. In the exemplary embodiment shown, the HMI 200 is an LCD display with a graphical user interface (GUI) 201, a detail display 202 and an adjustment display 203. The GUI 201 displays scanned images of an area of interest, as well as details such as time, date, and scale. In further exemplary embodiments, the GUI 201 may be configured to display multiple images and overlay images. In some embodiments, the GUI 201 may be a touch screen.

The detail display 202 is configured to give specific information in an easy-to-read format. For example, in the current embodiment, the detail display 202 is shown displaying the battery life and the current magnification. Both of these details are important to monitor while using the image analyzer 100 in the field. In further exemplary embodiments, the detail display 202 may be configured to display additional or alternative details, including, but not limited to, declination of the array assembly 73, distance from a surface of interest, remaining battery life (in minutes), the status of specific sensors (i.e., if any sensor is malfunctioning), progress of a current scan and combinations thereof.

In the exemplary embodiment shown, the adjustment display 203 includes selectable options for a variety of features of the surface deformation image analyzer 100 including a power button 204, a save button 205, a reset button 206, an adjust display button 207, a freeze button 208, a test sensor selector 209, a zoom dial 210, a scan speed selector 211 and an image/data selector 212. In further exemplary embodiments, the adjustment display 203 may include additional or fewer selectable options. In still further exemplary embodiments, the adjustment display 203 may be a touch screen; thereby, allowing for additional customization.

In the exemplary embodiment shown, the power button 204, the save button 205, the reset button 206, the adjust display button 207, the freeze button 208 are standard push button selectors known in the art. For example: pressing the power button 204 cycles power; pressing the save button 205 saves current scan data; pressing the reset button 206 resets the GUI 201 (without interfering with saved data); pressing the adjust display button 207 allows a user to alter the view on the GUI and move the image around without closing the form; and pressing the freeze button 208 disables the testing sequence offered by the test sensor selector 209.

In the exemplary embodiment shown, the test sensor selector 209 is used to test the sensor arrays 20, 30, 40 and 50. Each array 20, 30, 40 and 50 is selectable for individual testing. When going through a testing sequence, each sensor 22, 32, 42 and 52 in an array 20, 30, 40 and 50, respectively, is tested in sequence. In the exemplary embodiment shown, an indicator light in the center of the sensor selector 209 illuminates green at the completion of successful testing of an array 20, 30, 40 and 50. If a sensor fails, the sensor selector 209 illuminates red. In some embodiments, the GUI 201 may guide a user through troubleshooting or repair if a sensor fails testing.

The zoom dial 210 allows a user to select magnification. In the exemplary embodiment shown, the zoom dial 210 allows adjustable magnification up to nine times. In further exemplary embodiments, magnification may be increased or decreased on a continual scale or adjusted using a structure other than a positionable dial.

Similarly, the scan speed selector 211 allows a user to adjust the scan speed. The selector 211 is dependent on the speed of an initial scan by which the selector establishes as "normal." Further scans may be adjusted faster or slower than the initial scan. In further exemplary embodiments, scan speed may be selected using a structure other than a dial and scan speed may be continually adjustable along a continuum. In still further exemplary embodiments, scan speed may be provided in specific speeds of inches per second or centimeters per second.

The image/data selector 212 allows a user to select the image displayed on the GUI 201. For example, images collected from the arrays 20, 30, 40 and 50 may be viewed independently of each other or fused or layered over one another. Pressing the reset button 206 clears displayed images.

While in the exemplary embodiment shown, various dials and press buttons are used to allow a user to select between various functions and views offered by the surface deformation image analyzer 100. In further exemplary embodiments, different structures which allow a user to select functions may be used. For example, touch screens, knobs, slides, toggles, and combinations of these and other structures may be used.

Figure 4A:
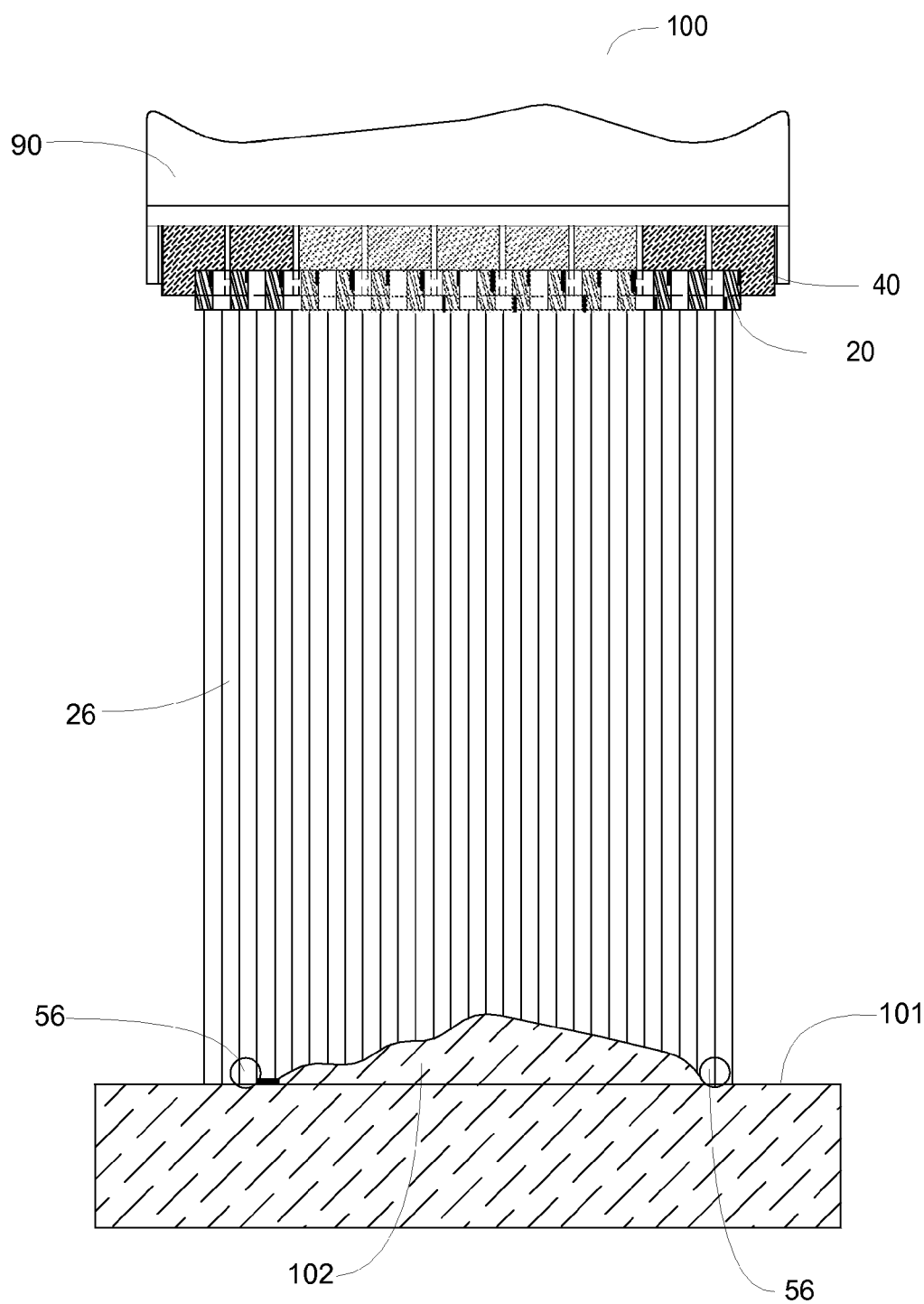
FIG. 4A is an exemplary embodiment of the surface deformation image analyzer scanning a deformation which is a protrusion.
Figure 4B:
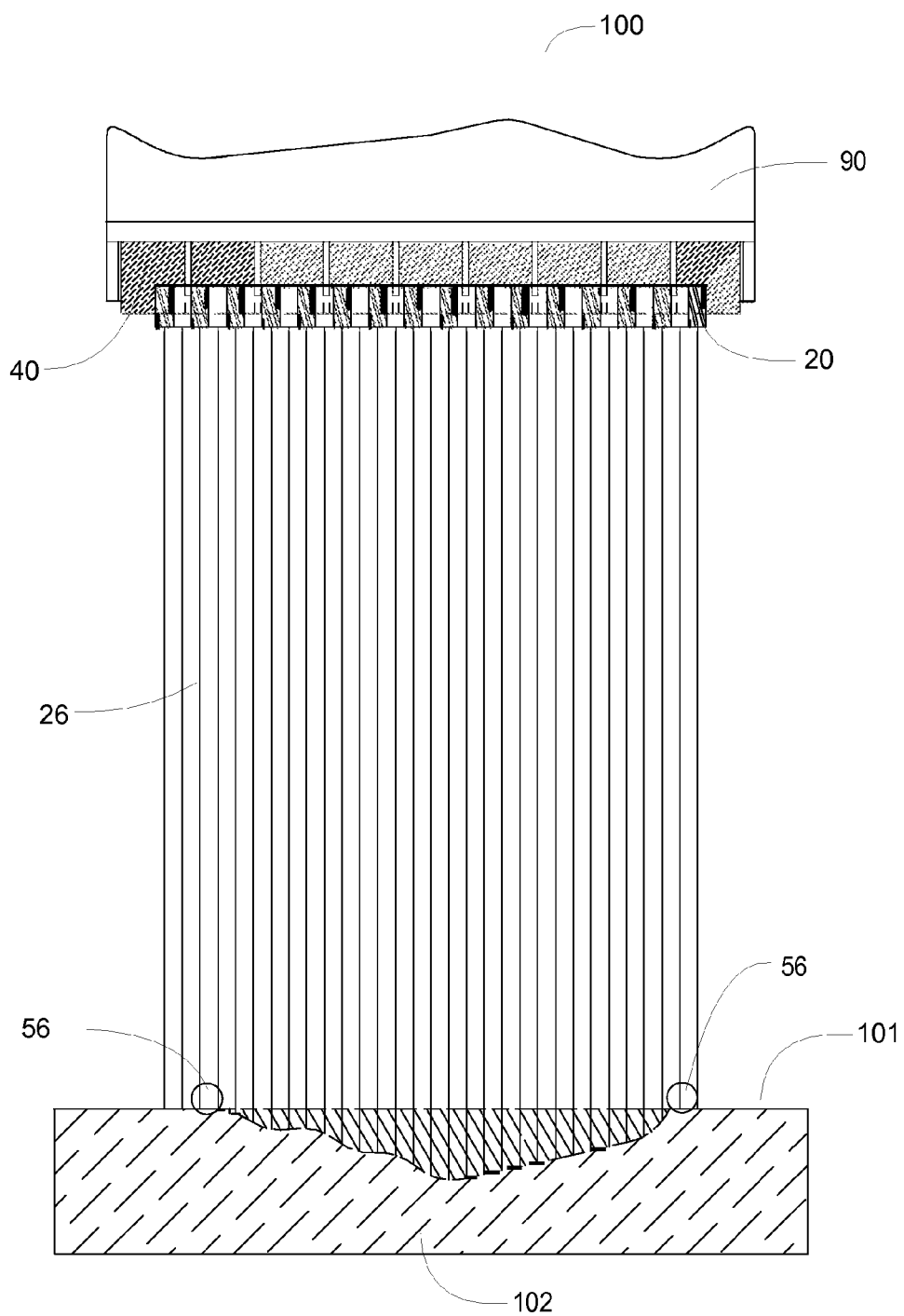
FIG. 4B is an exemplary embodiment of the surface deformation image analyzer scanning a deformation which is an intrusion.

FIG. 4A and FIG. 4B illustrate the surface deformation image analyzer 100 in use with different surface deformations. In the exemplary embodiment shown in FIG. 4A, a surface of interest 101 contains a deformation 102 which is a protrusion, while the surface of interest in FIG. 4B is shown with a deformation which is an intrusion.

In the exemplary embodiments shown, the displacement sensor array 20 and the ultrasonic sensor array 40 are visible on the bottom surface of the housing 90. The displacement sensors 22, which in the exemplary embodiment shown are laser displacement sensors, emit laser beams 26 which measure the displacement of the deformation 102. The displacement sensors 22 determine the amount of time for an emitted laser beam 26 to be reflected back to the displacement sensors in order to calculate the height or depth of the deformation 102.

The ultrasonic sensors 42 of the ultrasonic sensor array 40 emit ultrasonic acoustic emissions which are similarly reflected back to the ultrasonic sensors to provide additional detail not observable when using the displacement sensor array 20. For example, ultrasonic acoustic emissions are able to probe the depths and walls of minute openings which may otherwise be missed by using only the displacement sensor array 20. The ultrasonic sensor array 40 performs best when the surface of interest 101 is a hard surface. However, the ultrasonic sensor array 40 may be used when the surface of interest 101 is comparatively soft.

Also illustrated in FIG. 4A and FIG. 4B are ultraviolet markers 56. The ultraviolet markers 56 are UV-reflective markers. In the exemplary embodiments described, at least two ultraviolet markers 56 must be placed with the surface of interest 101 to allow proper overlay of the image generated by the ultraviolet image sensor array 50 over other images. In further exemplary embodiments, additional ultraviolet markers 56 may be used to increase the accuracy of image overlays. The ultraviolet markers 56 will register during a scan and become part of an image until calculations are completed.

Figure 5:
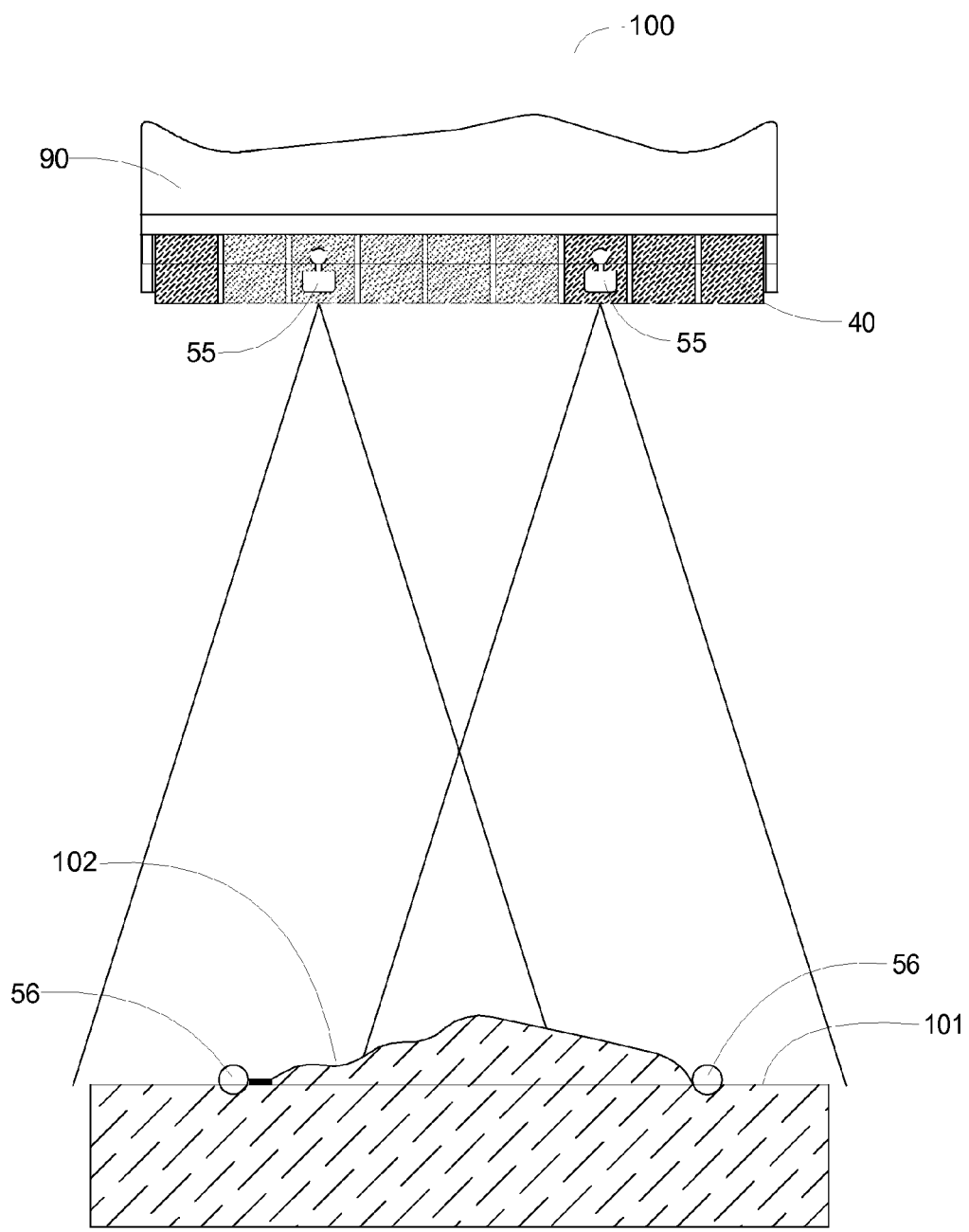
FIG. 5 is an exemplary embodiment of an ultraviolet sensor array of the surface deformation image analyzer scanning a deformation.

FIG. 5 illustrates an exemplary embodiment of the ultraviolet image sensor array 50 in more detail. In the exemplary embodiment shown, the ultraviolet LEDs 52 (not shown) and hidden by the ultrasonic sensor array 40, wash the surface of interest 101 with the deformation 102 in ultraviolet (UV) light. The digital cameras 55 are sensitive to ultraviolet light and photograph the surface of interest 101 as the array assembly 73 passes over the deformation 102.

The ultraviolet markers 56 are shown on the perimeter of the deformation 102. Because the ultraviolet markers 56 are UV-reflective, the digital cameras 55 will capture the location of the ultraviolet markers. The ultraviolet markers 56 are used as reference points when overlaying images generated by the sensor arrays 20, 30, 40 and 50.

Figure 6:
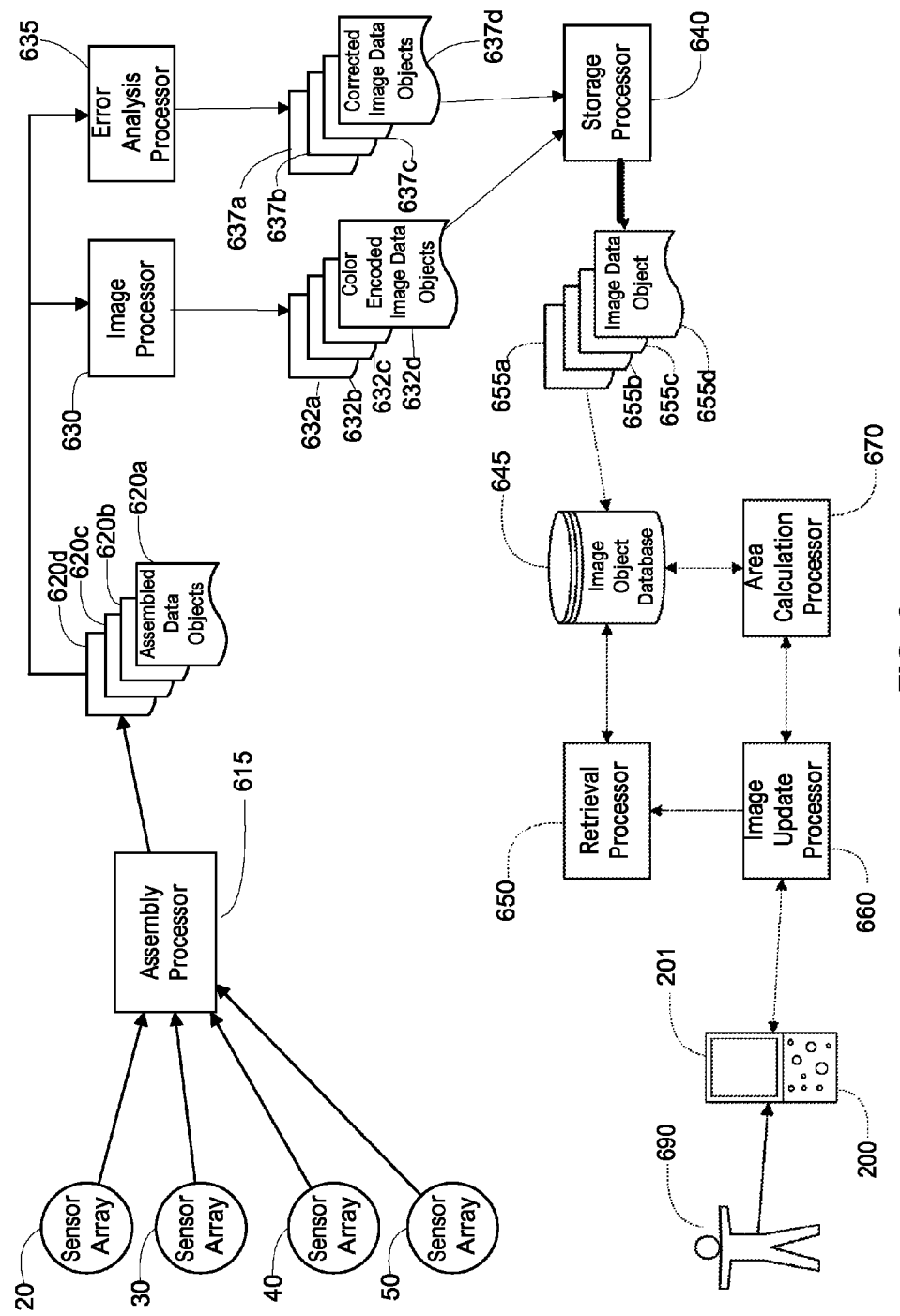
FIG. 6 is an exemplary embodiment of the processing components of the surface deformation image analyzer.

FIG. 6 is an exemplary embodiment of the processing components for the surface deformation image analyzer 100. The sensors arrays 20, 30, 40 and 50 perform a scan of a surface of interest. In the exemplary embodiments described, each sensor array 20, 30, 40 and 50 scans the area of interest simultaneously. However, in further exemplary embodiments, each sensor array 20, 30, 40 and 50 may be activated individually. In still further exemplary embodiments, a user may be able to select one or more of sensor arrays 20, 30, 40 and 50 in order to create a customized scan.

Information from each sensor array 20, 30, 40 and 50 is received by an assembling processor 615 which creates a plurality of quasi-unique data objects 620*a-d*, each data object containing attributes corresponding to the data sensed by one of the sensor arrays 20, 30, 40 and 50. In some exemplary embodiments, the data objects 620*a-d* are further processed by an image processor 630 and error analysis processor 635. The image processor 630 performs digital image processing techniques, such as image calibration, pixilation and other techniques known in the art, to produce color encoded image data objects 632*a-d*.

The error analysis processor 635 runs algorithms to remove or mitigate data abnormalities to produce corrected image data objects 637*a-d*. The color encoded image data objects 632*a-d* and image data objects 637*a-d* are then received by a storage processor 640 which processes the pairs of data objects (e.g., data objects from the processor 630 and a processor 640 containing attributes from the same sensor array) for storage in an image object database 645 as image data objects 655*a-d*.

While in the exemplary embodiment shown, the image processor 630 and the error analysis processor 635 operate simultaneously. In further exemplary embodiments, the processors 630 and 635 may operate in sequence. In still further exemplary embodiments, the error analysis processor 635 may be omitted or activated by a user request. In other exemplary embodiments, image processing and error analysis may be skipped or omitted. Quasi-unique data objects 620*a-d* are then relayed directly to the storage processor 640 for storage in the image object database 645 as image data objects 655*a-d*.

An image object retrieval processor 650 retrieves the image objects 620*a-d* and is configured with software to identify data attributes within images and to update the HMI 200 to display the image and quantitative values associated with the image and stored within the image objects as an attribute. For example, an image object 620*a* corresponding to information obtained through the displacement sensor array 20 may contain attributes such as the displacement values at any given point in a deformation region.

An image update processor 660 is configured with software to receive input from a user 690 and to communicate with the retrieval processor 650 to update the image on the HMI 200 based on user input. For example, the user 690 may request viewing the image generated by both the displacement sensor array 20 and the temperature sensor array 30 overlaid for comparison. The image update processor 660 receives the request and communicates with the retrieval processor 650 to retrieve the desired image objects and to create the composite image for display.

In the exemplary embodiment shown, the image data object 655*a* is laser displacement image data object. The image data object 655*a* contains attributes including, but not limited to, the quantitative displacement value at any given point in an area of interest, the change in displacement between given points in an area of interest and any other information which is sensed by the displacement sensor array 20.

The displacement image produced by the image data object 655*a* is displayed on the GUI 201 as a spectrogram image with areas of elevation and depression represented on a color spectrum (red, orange, yellow, green and blue). Using the HMI 200, a user can determine the exact displacement at a specific point in the image, as well as the coordinates of the point.

The image data object 655*b* is a laser temperature image data object. The image data object 655*b* contains attributes including, but not limited to, the quantitative temperature value at any given point in an area of interest, the change in temperature between given points in an area of interest and any other information which is sensed by the temperature sensor array 30. The thermal image produced by the image data object 655*b* shows variation in temperature as represented by graduated changes in the color spectrum (red, orange, yellow, green and blue). Using the HMI 200, a user can determine the exact temperature at a specific point in the image, as well as the coordinates of the point.

The image data object 655*c* is ultrasonic image data object. The image data objects 655*c* contains attributes including, but not limited to, ultrasonic reflection values at any given point in an area of interest, the difference in reflection values between points in an area of interest, and any other information which is sensed by the ultrasonic image sensor array 40. In the exemplary embodiments described, the acoustic image produced by the image data object 655*c* is displayed on the GUI 201 in a format almost identical to that of the displacement image—using the same color spectrum. The acoustic image will show minute imperfections in greater detail than the displacement image. In further exemplary embodiments, the acoustic image and displacement image may be differentiated by color spectrum or another visual cue.

The image data object 655*d* is an ultraviolet image data object. The image data object 655*d* contains attributes including, but not limited to: ultraviolet reflection values at any given point in an area of interest; the difference in reflection values between points in an area of interest; and any other information which is sensed by the ultraviolet sensor array 50. In the exemplary embodiments described, the UV image produced by the image data object 655d is displayed on the GUI 201 as a high-resolution scan image. Organic material lodged in a surface deformation is illuminated by the ultraviolet sensor array 50 and is displayed on the GUI 201 in the UV image. Because four separate image data objects are created (655a, 655b, 655c and 655d), and the image produced by each image data object 655a, 655b, 655c and 655d can be viewed individually or in combination with the others, there are sixteen possible image views for display on the GUI 201.

Also illustrated in FIG. 6 is an area calculation processor 670. The area calculation processor 670 runs algorithms using information stored in the image object database 645 in order to determine the area of a deformation region. Algorithms include, but are not limited to, Pick's theorem, Simpson's rule, a Monte Carlo method of quasirandom computation, and combinations of these algorithms. In some exemplary embodiments, user input may be used to help define a deformation region. The image update processor 660 receives user input and communicates with area calculation processor 670 to provide feedback from a user 690 regarding a deformation area. The image update processor 660 also updates the HMI 200 to display updated deformation area information.

Figure 7:
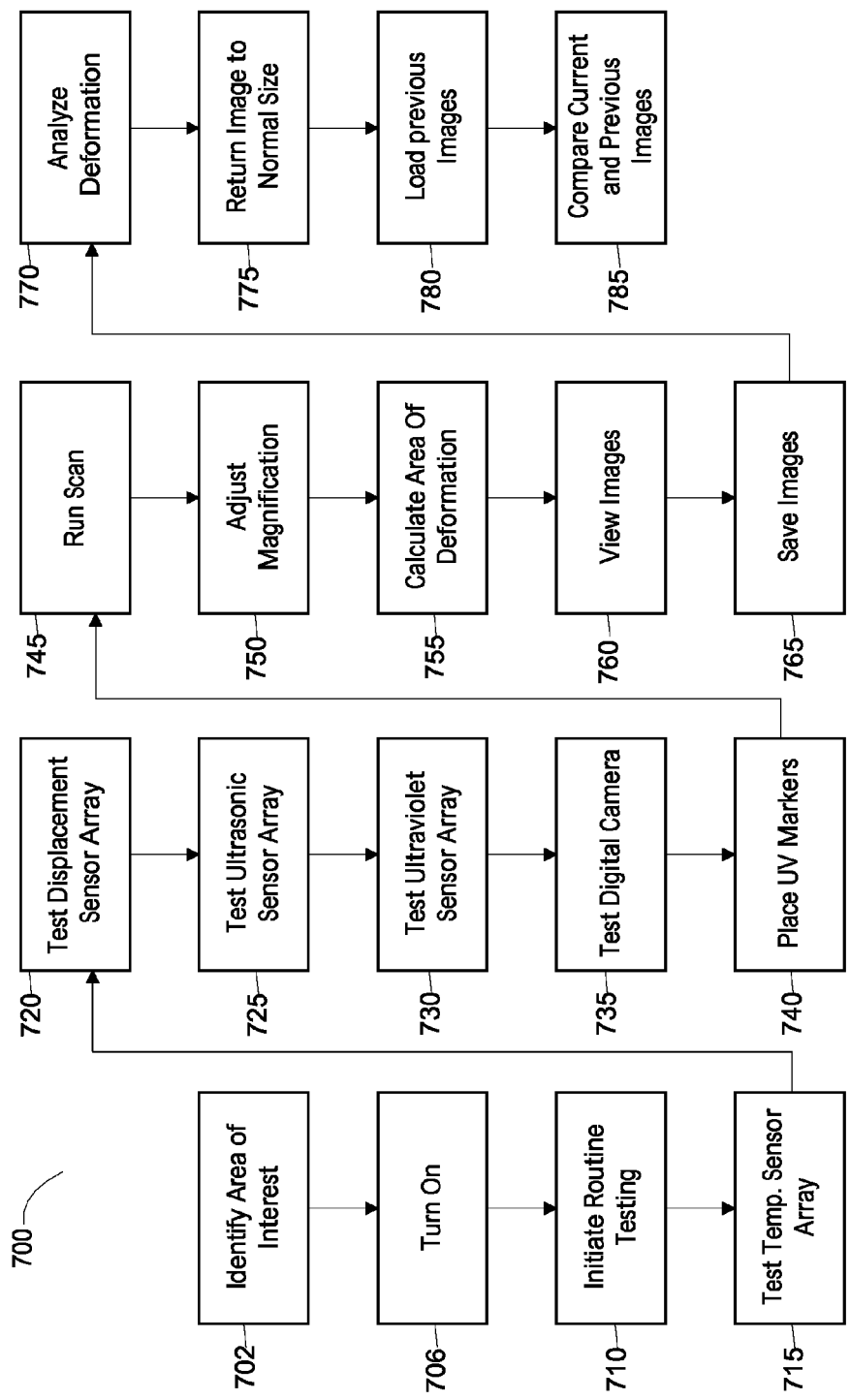
FIG. 7 is an exemplary operational flowchart for completing a scan using the surface deformation image analyzer.

FIG. 7 is an operational flow chart 700 for completing a scan using the surface deformation image analyzer 100. First, in step 702, an area of interest is identified and viewed for any visible deformity or medical complication. In step 706, once an area of interest is identified, the image analyzer 100 is turned on; thereby, supplying power to each sensor arrays 20, 30, 40 and 50. In step 710, a user initiates routine testing of each sensor array 20, 30, 40 and 50. In further exemplary embodiments, testing may start automatically when the image analyzer 100 is turned on.

In the exemplary embodiment shown: the temperature sensors 32 of the temperature sensor array 30 are tested first in step 715; followed by testing of the displacement sensors 22 in step 720; followed by testing of the ultrasonic sensors (transducers) 42 in step 725; and followed by testing of the ultraviolet LEDs 52 and the digital cameras 55 of the ultraviolet sensor array 50 in steps 730 and 735, respectively. In further exemplary embodiments, testing of the sensor arrays 20, 30, 40 and 50 may be completed in any order or in an order specified by a user. In still further exemplary embodiments, one or more of the steps 715, 720, 725, 730 and 735 may be performed simultaneously.

In conducting the tests in steps 715, 720, 725, 730 and 735, each sensor in the respective arrays is tested in sequence. If any sensor fails, the image analyzer 100 is turned off and on again (step 706), and the testing sequence of steps 715, 720, 725, 730 and 735 is repeated until all sensor pass testing. If any sensor continues to fail testing, the GUI 201 may prompt a user to complete repairs on a particular sensor prior to using the image analyzer 100. Once all sensors pass testing, at least two ultraviolet markers 56 are placed on the area of interest (step 740). The ultraviolet markers 56 are used to properly overlay images. After the ultraviolet markers 56 are placed; the scan is run (step 745).

In step 750, the magnification of the image displayed on the screen is adjusted. It is desirable to enlarge an area of interest so that the area fills the display screen and the ultraviolet markers 56 are still visible. Depending on the HMI 200, magnification may be adjusted using the GUI 201 or a hardware selector (e.g., dial, slide, etc.).

Next, in step 755, the area of the deformation is calculated. In calculating the area of the deformation, the surface deformation image analyzer 100 applies Simpson's rule to the closed deformation shape—whether the shape is regular or irregular. To calculate the area of the deformation, using the HMI 200; a user selects a number of points around the perimeter of the deformation. The points are connected with straight lines to create a polygon or any other geometric form, depending on the shape of the deformity, around the deformation. The image analyzer 100 generates a grid which overlays the polygon. The grid specifies the units of measurement and may be in inches, centimeters, or any other unit appropriate for the deformation.

The entire area of the polygon is then calculated using Pick's theorem. Pick's theorem calculates the area (A) of a polygon based on the number of grid points located in the interior of the polygon (i) and the number of grid points located on the polygon's perimeter (b) by using the following equation:

$$\text{Area} = r^2 \left( i + \frac{b}{2} - 1 \right)$$

where r is the scaling factor measuring the spacing between grid points.

Simpson's rule is then used to calculate the areas of any non-deformation regions included in the polygon that are formed by a simple closed polynomial curve. Simpson's rule may be written as $$\text{Area} = \int_a^b f(x)\,dx \approx \frac{h}{3}[y_0 + 4y_1 + 2y_2 + \ldots + 4y_{n-1} + y_n]$$

where $y_i$ are variable heights lying perpendicular to the x axis and $$h = \frac{b-a}{n}$$

is the length of the curve divided into even numbered partitions.

For some non-deformation regions, the area must be rotated to form a simple closed polynomial curve. For rotated curves, when variable heights ($x_1$) lie perpendicular to the y axis, Simpson's rule can be written as $$\text{Area} = \int_c^d f(y)\,dy \approx \frac{h}{3}[x_0 + 4x_1 + 2x_2 + \ldots + 4x_{n-1} + x_n]$$

where $$h = \frac{d-c}{n}$$

is the length of the curve divided into n even numbered partitions.

If a non-deformation region, after rotation and if necessary, has a shape such that a vertical line drawn over the curve would cross over open space, the region must be subdivided and the subdivided regions rotated. Small non-deformation regions may be ignored. In some instances, when the area of a deformation may be approximated by just the area of a polygon calculated by Pick's theorem, or subdivided into multiple polygons—the area of which add to an approximation of the deformation area, additional calculations using Simpson's rule may be omitted. For example, a crack in a hard surface may have primarily straight lines around the perimeter, and the area may be approximated using only Pick's theorem.

FIGS. 8A-8D illustrate an exemplary deformation, deformation polygon having an area calculated by Pick's theorem, and non-deformation regions having areas calculated by Simpson's rule. A user will determine the points for forming the polygon for applying Pick's theorem, any non-deformation regions requiring the application of Simpson's rule (as well as those regions considered too small), and any non-deformation regions that must be subdivided for applying Simpson's rule. In some exemplary embodiments, a Monte Carlo method of quasi-random computation may be used in place of Simpson's rule to calculate the area under an irregular curve. After each non-deformation region area is calculated, the areas are totaled and subtracted from the area of the polygon calculated using Pick's theorem. The resulting value will be a close approximation of the area of the deformation.

In the exemplary embodiment described, the area of a deformation is calculated using the image generated by the ultraviolet sensor array 50 and captured by the digital cameras 55. In step 760, the HMI 200 may be used to call up images captured by individual sensor arrays or different overlay combinations of those images. Desired images, or overlaid images, are saved in step 765. In step 770, the deformation may be analyzed using the HMI 200. For example, the HMI 200 may be used to determine displacement and temperature values of certain points in the deformation, or general comparisons and other measurements may be noted.

In some exemplary embodiments, the surface deformation image analyzer 100 may be used to track repairs or healing of deformations, or otherwise compare the effect of time on a deformation. When comparing current scanned data to previously scanned data for the same deformation; the images must first be returned to normal size (step 775). In step 780, the previous images are loaded (e.g., from internal memory, removable memory or remote memory) and compared to the current images (step 785). In some exemplary embodiments, the current and past images may be overlaid for direct visual comparison and the overlaid images saved.

Figure 8B:
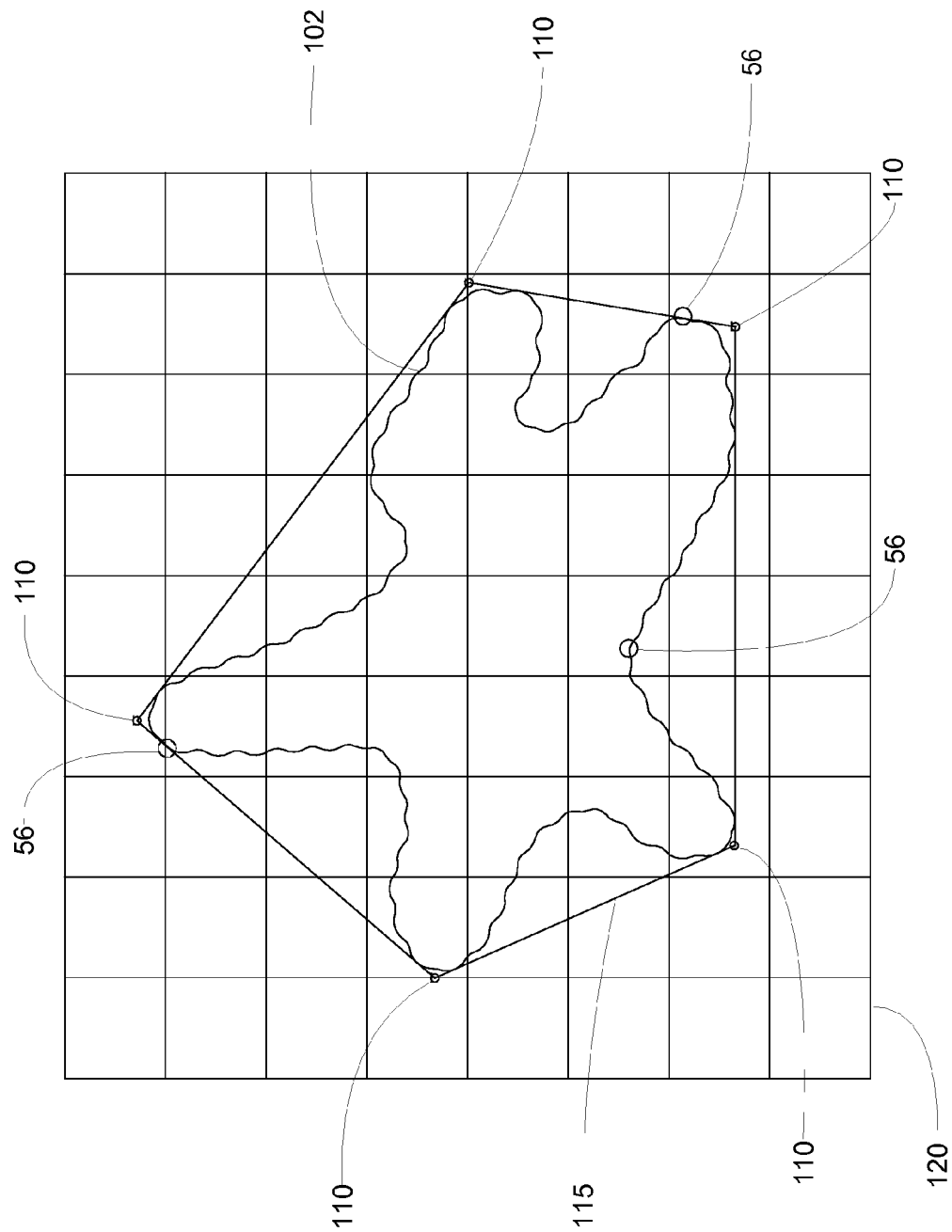
FIG. 8B is an exemplary embodiment of a polygon formed around the irregular deformation used to calculate the area of the deformation using Pick's theorem.

FIG. 8A illustrates an irregular deformation 102 on the surface of interest 101. FIG. 8B shows the deformation 102 with points 110 marked on the perimeter of the deformation creating a polygon 115. A grid 120 is overlaid on the polygon 115 and used to calculate the area of the polygon using Pick's theorem.

Figure 8C:
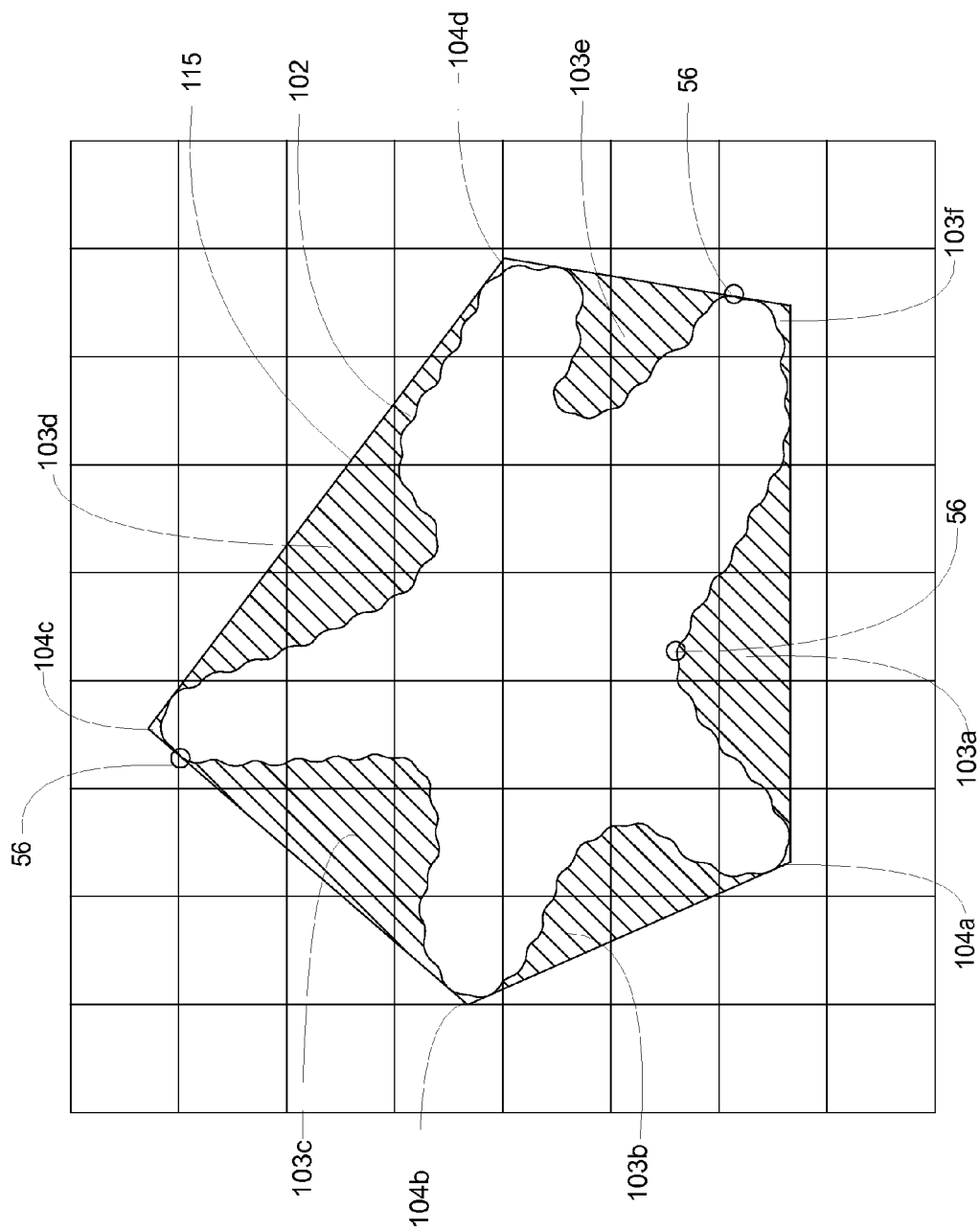
FIG. 8C is an exemplary embodiment of non-deformation regions having an area which may be calculated using Simpson's rule.

FIG. 8C illustrates the deformation 102 with the polygon 115. Non-deformation regions 103a-f and 104a-d are shown as primarily closed polynomial curves. In the exemplary embodiment shown, the non-deformation regions 104a-d are considered too small to impact an overall area calculation, while the non-deformation regions 103a-e have areas which are calculated using Simpson's rule. In the exemplary embodiment shown, the non-deformation region 103a is oriented along the x-axis and does not need to be rotated for calculation, while the remaining the non-deformation region 103b-f will need to be rotated for calculation.

Figure 8D:
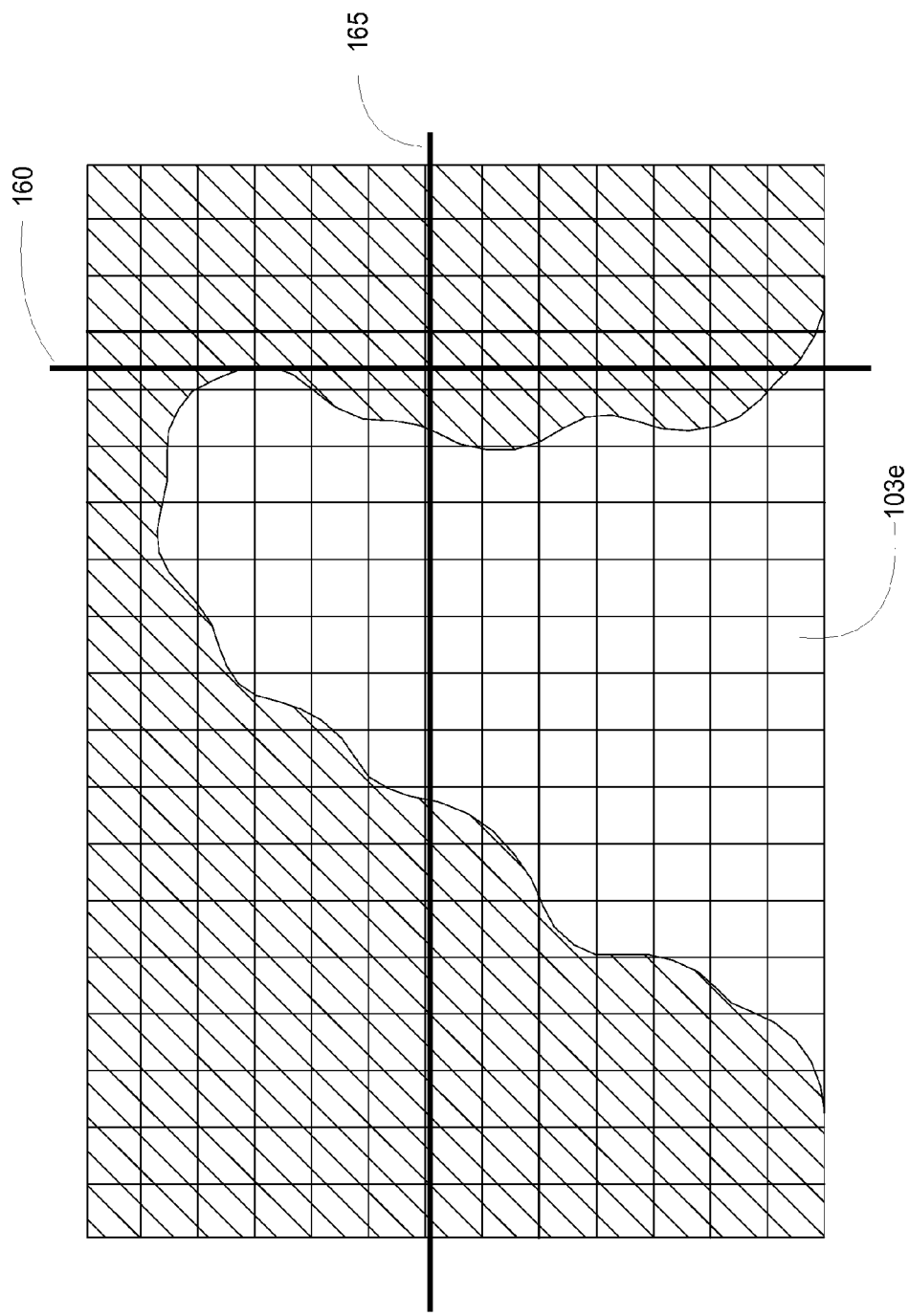
FIG. 8D is an exemplary non-deformation region which is rotated and subdivided prior to calculating the area using Simpson's rule.

As illustrated in FIG. 8D, when the non-deformation region 103e is rotated so that the edge defined by the polygon 115 is along the x-axis, a vertical line 160 exists that passes through open space. The non-deformation region 103e will need to be subdivided into two separate portions, such as along line 165, in order to calculate the area using Simpson's rule. The two portions of non-deformation region 103e may then be rotated along the y-axis for applying Simpson's rule. In further exemplary embodiments, a non-deformation region may be subdivided or partitioned using a single or multiple vertical or horizontal lines. In still further exemplary embodiments, a non-deformation region may be subdivided using a combination of vertical and horizontal lines.

It will be understood that many additional changes in the details, materials, steps and arrangement of parts, which have been herein described and illustrated in order to explain the nature of the invention, may be made by those skilled in the art within the principle and scope of the invention as expressed in the appended claims.

What is claimed is:

1. A surface deformation image analyzer apparatus comprising:
   a display panel;
   a control panel;
   a housing having an upper surface and a movable lower surface, wherein the lower surface is selectively movable within a range of 0 to 50 degrees by an adjustment element and wherein said display panel and said control panel are attached to the upper surface;
   a displacement sensor array containing a plurality of displacement sensors in a parallel configuration;
   a temperature sensor array containing a plurality of temperature sensors in a parallel configuration;
   an ultrasonic sensor array containing a plurality of ultrasonic transducers in a parallel configuration;
   an ultraviolet image sensor array containing a plurality of ultraviolet LEDs in a parallel configuration and at least two ultraviolet-sensitive cameras interposed between said ultraviolet LEDs;
   at least two scanner belts;
   an array assembly containing said displacement sensor array, said temperature sensor array, said ultrasonic sensor array and said ultraviolet sensor array wherein said displacement sensor array, said temperature sensor array, said ultrasonic sensor array and said ultraviolet sensor array are parallel to each other with said array assembly movable on said scanner belts at a speed to scan of an area of interest;
   at least one hardware processing component configured with software to receive sensor input from said displacement sensor array, said temperature sensor array, said ultrasonic sensor array and said ultraviolet sensor array and configured to transform the sensor input to create a plurality of data objects;
   an image area hardware processing component configured with at least one algorithm to define a deformation area from the area of interest;
   an image storage processing component configured to store image objects in an image object database;
   an image object retrieval hardware processing component configured to retrieve the image objects, to identify data attributes within the image objects and to display quantitative values stored within the image objects; and
   an input processing component configured to accept input from said control panel and to update said display panel.

2. The apparatus of claim 1 wherein said displacement sensors are arranged in an order of sequential activation.

3. The apparatus of claim 2 wherein each of said ultrasonic transducers has a unique operating frequency.

4. The apparatus of claim 3 wherein said housing includes at least two handles attached to an exterior of said housing.

5. The apparatus of claim 4 wherein said scanner belts are half rotational belts.

6. The apparatus of claim 5 wherein said image object retrieval hardware processing component is configured with software to access historic data and to compare the image object to the historic data.

7. The apparatus of claim 6 wherein said at least one image area hardware processing component is configured with software to calculate the deformation area.

8. The apparatus of claim 7 wherein a sequential activation of said displacement sensors and the speed of said scanner belts are coordinated.

9. The apparatus of claim 8 wherein temperature readings from each temperature sensor are capable of producing a spectrographic image.

10. The apparatus of claim 9 wherein each of said displacement sensor array, said temperature sensor array, said ultrasonic sensor array and said ultraviolet sensor array are selectable for individual testing.

11. The apparatus of claim 10 wherein the speed of said scanner belts is adjustable.

\* \* \* \* \*